(12) United States Patent
Dhawan et al.

(10) Patent No.: US 8,163,955 B2
(45) Date of Patent: *Apr. 24, 2012

(54) PROCESS FOR THE SYNTHESIS OF 2,6-DIAMINO-3,5-DINITROTOLUENE

(75) Inventors: Rajiv Dhawan, Wilmington, DE (US); Joachim C. Ritter, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/634,767

(22) Filed: Dec. 10, 2009

(65) Prior Publication Data

US 2010/0160678 A1 Jun. 24, 2010

Related U.S. Application Data

(60) Provisional application No. 61/138,662, filed on Dec. 18, 2008.

(51) Int. Cl.
*C07C 211/00* (2006.01)
(52) U.S. Cl. ........ 562/441; 564/305; 564/306; 564/415; 564/416; 562/480
(58) Field of Classification Search .................. None
See application file for complete search history.

(56) References Cited

U.S. PATENT DOCUMENTS 3,174,947 A * 3/1965 Marvel et al. ................. 528/331
3,476,590 A 11/1969 Rabilloud et al.
3,783,137 A * 1/1974 Gerber et al. ................. 528/208

FOREIGN PATENT DOCUMENTS

JP 2003-292475 10/2003
JP 2005-330470 12/2005

OTHER PUBLICATIONS

Boyer et al, Journal of the American Chemical Society, 1960, 82, 2213-15.*
Knoblock et al, Chemische Berichte, 1958, 91, 2562-6.*
Blanksma, Nitro Derivatives of 2,6-Dibromotoluene, Chemisch Weekblad, 1913, vol. 9, pp. 968-973, Abstract Only.
Knobloch et al., Synthesis of 2.6-Disubstituted Benzo (1.2.4.5) Bisimidazol, Chemische Berichte, 1958, vol. 91, pp. 2562-2565 (Machine Translated).
Boyer et al., The Preparation of 6,7-Disubstituted Quinoxalines, JACS, 1960, vol. 82, pp. 2213-2215.
Ritter et al., U.S. Appl. No. 61/138,602, filed Dec. 18, 2008.
Ritter et al., U.S. Appl. No. 61/138,615, filed Dec. 18, 2008.
Dhawan et al., U.S. Appl. No. 61/138,626, filed Dec. 18, 2008.
Dhawan et al., U.S. Appl. No. 61/138,678, filed Dec. 18, 2008.
Dhawan et al., U.S. Appl. No. 61/138,651, filed Dec. 18, 2008.
Ritter. U.S. Appl. No. 61/138672, filed Dec. 18, 2008.
Dhawan et al., U.S. Appl. No. 61/138,696, filed Dec. 18, 2008.
Cotton and Wilkinson, Advanced Inorganic Chemistry, Periodic Table Only, 1966, Interscience Publishers, $2^{nd}$ Edition, New York.

* cited by examiner

*Primary Examiner* — Sudhakar Katakam

(57) ABSTRACT

An improved process is provided for the preparation of 2,6-diamino-3,5-dinitrotoluene by amination of 2,6-dichloro-3,5-dinitrotoluene. The presence of water unexpectedly results in a highly pure product, free of glycol ether impurities. This product can be used to make highly pure 2,3,5,6-tetraaminotoluene, which in turn can be used to make high molecular weight polybenzimidazoles for high strength fibers.

5 Claims, No Drawings

PROCESS FOR THE SYNTHESIS OF 2,6-DIAMINO-3,5-DINITROTOLUENE

This application claims priority under 35 U.S.C. §119(e) from, and claims the benefit of, U.S. Provisional Application No. 61/138,662, filed Dec. 18, 2008, which is by this reference incorporated in its entirety as a part hereof for all purposes.

TECHNICAL FIELD

The disclosure relates to a method of making 2,6-diamino-3,5-dinitrotoluene, which may be used in the manufacture of dyes, pharmaceuticals and polymers.

BACKGROUND

The compound 2,6-diamino-3,5-dinitrotoluene ("DADNT") (I),

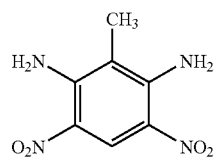

I may be used as a starting material or intermediate in the preparation of a variety of products, which include dyes, pharmaceuticals, and monomers for incorporation into polybenzimidazole polymers.

The preparation of DADNT has been reported by J. J. Blanksma, in "Nitro Derivatives of 2,6-Dibromotoluene," Chemisch Weekblad 9, 968-973 (1913). The starting material was 2,6-dibromotoluene, which was dinitrated and reacted under pressure with $NH_3$ at 150° C. This process has limited commercial viablity because of the high cost of 2,6-dibromotoluene. Furthermore, the brominated intermediates produced in this process are highly skin sensitizing chemicals and would not allow for low cost production in a commercial setting because of environmental and handling issues.

High purity DADNT is useful as a precursor to high-purity 2,3,5,6-tetraaminotoluene ("TAT") (Formula II),

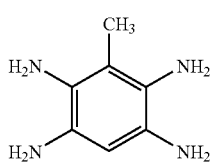

II which may be used as a precursor to high-performance polymers such as polybenzimidazoles, which are used to make high-performance, high-strength fibers. The purity of the precursors affects the polymer molecular weight that can be achieved, which in turn determines whether satisfactory fibers can be produced.

A need thus remains for a process for making 2,6-diamino-3,5-dinitrotoluene with higher selectivity and purity.

SUMMARY

In one embodiment, this invention provides a process for preparing 2,6-diamino-3,5-dinitrotoluene (Formula I),

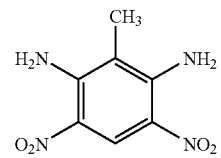

I comprising, under exclusion of oxygen, providing a reaction mixture comprising a suspension of 2,6-dihalo-3,5-dinitrotoluene (Formula III)

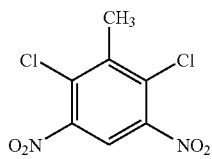

III in glycol in the presence of ammonia and about 2 to about 25 wt % water, and heating the reaction mixture to convert the 2,6-dichloro-3,5-dinitrotoluene to 2,6-diamino-3,5-dinitrotoluene.

In another embodiment, this invention provides an integrated process for preparing a complex of 2,3,5,6-tetraaminotoluene and the aromatic diacid XYTA, wherein the complex is generally described by Formula IV

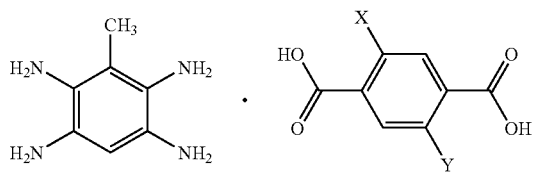

IV wherein X and Y are each independently selected from the group consisting of H, OH, SH, methyl, ethyl, F, Cl, and Br; comprising the sequential steps under exclusion of oxygen:
a) nitration of 2,6-dichlorotoluene (V)

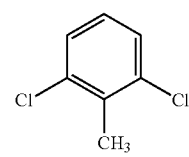

V in a reaction mixture comprising oleum or $SO_3$, nitric acid, and $H_2SO_4$
wherein
(i) the concentration of nitric acid is about 2.0 to about 2.3 moles per mole of 2,6-dihalotoluene;
(ii) the concentration of $SO_3$ is about 1 to about 3 moles per mole of 2,6-dichlorotoluene;
(iii) the concentration of 2,6-dichlorotoluene in the reaction mixture is between about 12 and about 24 weight percent; and
wherein the temperature of the reaction mixture does not exceed 120° C.; thereby producing 2,6-dichloro-3,5-dinitrotoluene;

b) directly separating the 2,6-dichloro-3,5-dinitrotoluene from the reaction mixture by filtration, while recycling the sulfuric acid mother liquor;

c) washing the 2,6-dichloro-3,5-dinitrotoluene with water or acid then water, then with $NH_4OH$;

d) aminating the 2,6-dichloro-3,5-dinitrotoluene by forming a reaction mixture comprising a suspension of the 2,6-dichloro-3,5-dinitrotoluene in glycol in the presence of ammonia and about 2 to about 25 wt % water, and heating the reaction mixture to convert the 2,6-dichloro-3,5-dinitrotoluene to 2,6-diamino-3,5-dinitrotoluene;

e) directly separating the 2,6-diamino-3,5-dinitrotoluene from the reaction mixture formed in step (d) by filtration, washing with glycol, then washing with water;

f) forming a slurry of the 2,6-diamino-3,5-dinitrotoluene with water and transferring the slurry to a hydrogenation reactor containing a hydrogenation catalyst to form a reaction mixture;

g) hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. to hydrogenate the 2,6-diamino-3,5-dinitrotoluene, thereby producing 2,3,5,6-tetraaminotoluene;

h) contacting the 2,3,5,6-tetraaminotoluene produced in (g) with an aqueous solution comprising 1 to 6 equivalents of acid per mol of 2,3,5,6-tetraaminotoluene, optionally heating the solution, thereby dissolving the 2,3,5,6-tetraaminotoluene;

i) filtering the reaction mixture, thereby removing the spent hydrogenation catalyst;

j) combining the filtered reaction mixture with
  (i) 0 to 5 equivalents of an acid;
  (ii) 0 to 5 equivalents of an organic base or an inorganic base;
  (iii) optionally, a buffer solution; and
  (iv) an XYTA source selected from XYTA and $M_2XYTA$ (Formula VI)

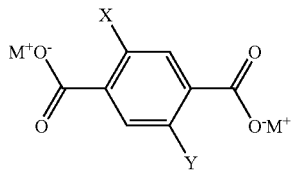

wherein M is K or Na,
and wherein the molar ratio of XYTA to the 2,3,5,6-tetraaminotoluene salt is from 1:1 to 1:1.1;

thereby adjusting the pH of the mixture to between about 3 and about 10 and thereby producing and precipitating the complex generally described by Formula (IV); and k) cooling, filtering, and washing the precipitated complex.

DETAILED DESCRIPTION

The following description is exemplary and explanatory only and is not restrictive of the invention, as defined in the appended claims.

In the context of this disclosure, a number of terms shall be utilized.

As used herein the term "wt % water" refers to the weight % of water based on glycol, i.e., 100*the weight of weight/(weight of glycol+weight of water) in the reaction mixture.

As used herein, the term "TAT salt" or, equivalently, "2,3,5,6-tetraaminotoluene salt", denotes a compound formed by reaction of 2,3,5,6-tetraaminotoluene with an acid such as HCl, acetic acid, $H_2SO_4$, or $H_3PO_4$. One example of a TAT salt is TAT.4HCl.

As used herein, the term "XYTA" denotes 2-X-5-Y-terephthalic acid, where X and Y each independently selected from the group consisting of H, OH, SH, methyl, ethyl, F, Cl, and Br. One example is 2,5-dihydroxyterephthalic acid, in which X=Y=OH. The disodium or dipotassium salt of the diacid is represented by the term "$M_2XYTA$" where M is Na or K.

As used herein, the term "oleum" denotes fuming sulfuric acid, which is anhydrous and is formed by dissolving excess sulfur trioxide ($SO_3$) into sulfuric acid.

As used herein, the term "fuming nitric acid" denotes concentrated nitric acid containing dissolved nitrogen dioxide.

As used herein, the term "net yield" of a product denotes the actual, in-hand yield, i.e., the theoretical maximum yield minus losses incurred in the course of activities such as isolating, handling, drying, and the like.

As used herein, the term "purity" denotes what percentage of an in-hand, isolated sample is actually the specified substance.

Unexpectedly, we have found that the presence of even a small amount of water during the amination process results in a higher purity DADNT product.

In one embodiment, a process is provided for preparing 2,6-diamino-3,5-dinitrotoluene, comprising, under exclusion of oxygen, providing a reaction mixture comprising a suspension of 2,6-dichloro-3,5-dinitrotoluene, "DCDNT" (Formula III)

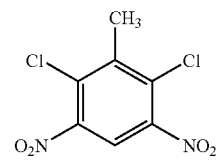

in glycol in the presence of ammonia and about 2 to about 25 wt % water, and heating the reaction mixture to convert the 2,6-dichloro-3,5-dinitrotoluene to 2,6-diamino-3,5-dinitrotoluene.

The DCDNT may be prepared, for example, by nitration of 2,6-dichlorotoluene as described in European Patent Application 237,955 A2, or according to the method described in co-pending U.S. Provisional Application No. 61/138,672, which is by this reference incorporated in its entirety as a part hereof for all purposes.

In another embodiment of the process, the suspension contains about 10 to about 25 wt % 2,6-dichloro-3,5-dinitrotoluene ("DCDNT," Formula III) in a mixture of glycol and about 2 to about 25 wt % water; and the suspension is heated to a temperature in the range of about 100° C. to about 160° C. and contacted with gaseous $NH_3$, for a time sufficient to convert the 2,6-dichloro-3,5-dinitrotoluene to 2,6-diamino-3,5-dinitrotoluene. More specifically, the suspension is heated to a temperature in the range of about 100° C. to about 160° C., preferably about 140° C., to dissolve the 2,6-dichloro-3,5-dinitrotoluene in the glycol. The resulting solution is contacted at that temperature with gaseous $NH_3$ for approximately four to eight hours close to ambient pressure; the gaseous NH₃ is fed as it is consumed.

In a further embodiment of the process, the suspension contains about 10 to about 25 wt % 2,6-dichloro-3,5-dinitrotoluene ("DCDNT," Formula III) in glycol; the suspension is heated to a temperature in the range of about 100° C. to about 160° C. and contacted with an aqueous ammonia solution to form a reaction mixture. The reaction mixture is heated to a temperature in the range of about 100° C. to about 160° C. for a time sufficient to convert the 2,6-dichloro-3,5-dinitrotoluene to 2,6-diamino-3,5-dinitrotoluene. More specifically, the reaction mixture is heated to a temperature in the range of about 100° C. to about 160° C., preferably about 140° C., to dissolve the 2,6-dichloro-3,5-dinitrotoluene in the glycol. The resulting solution is contacted at that temperature with aqueous ammonia (typical concentration, about 28 wt % NH₃) for approximately four to eight hours close to ambient pressure; the aqueous ammonia is fed as it is consumed. The aqueous ammonia solution is added such that the amount of NH₃ released through the gas outlet is kept at minimum and stirring is kept constant throughout the reaction. During addition of the aqueous ammonia solution, the amount of water in the reaction mixture increases from about 2% to about 25 wt % based on glycol.

In this embodiment, the amount of water, initially about 2 wt % based on glycol, increases steadily up to about 17% at reaction completion. Since the glycol ether byproduct forms only at high conversions, the amount of water added is sufficient. An advantage to this embodiment is that one can use an aqueous solution of ammonia (also referred to as ammonium hydroxide or "NH₄OH") which is easier to handle and less hazardous than gaseous ammonia. Reaction rates are also be higher when an aqueous solution of ammonia is used.

In another embodiment, rather than (as described above) forming a suspension of DCDNT in glycol and water and then feeding gaseous ammonia, or forming a suspension of DCDNT in glycol and then feeding an aqueous solution of ammonia, the DCDNT is instead contacted with a feed stream containing glycol, water and NH₃, thereby forming the reaction mixture. This allows for easy adjustment of the relative proportions of glycol, water, and NH₃ at any time during the amination process. In this embodiment, the reaction mixture so formed is then heated to a temperature in the range of about 100° C. to about 160° C. for a time sufficient to convert the 2,6-dichloro-3,5-dinitrotoluene to 2,6-diamino-3,5-dinitrotoluene (Formula I). More specifically, the reaction mixture is heated to a temperature in the range of about 100° C. to about 160° C., preferably about 140° C., to dissolve the 2,6-dichloro-3,5-dinitrotoluene. The reaction mixture is heated for approximately four to eight hours, close to ambient pressure.

In any of the above embodiments, at reaction completion, the 2,6-diamino-3,5-dinitrotoluene thereby produced is filtered, typically at about 60° C., and washed with glycol and then water. The mother liquor (filtrate) containing glycol can be collected and the glycol distilled and recycled; when this is done, purges are drawn to prevent accumulation. The wet cake of 2,6-diamino-3,5-dinitrotoluene can be dried if it is the final product. Alternatively, it can be slurried with water as a suspension and transferred to a hydrogenation reactor for producing 2,3,5,6-tetraaminotoluene ("TAT").

In yet another embodiment, the process further comprises hydrogenating the 2,6-diamino-3,5-dinitrotoluene by contacting it with and a hydrogenation catalyst hydrogen at a pressure in the range of about 0.31 to about 3.45 MPa and a temperature in the range of about 20° C. to about 100° C. for sufficient time to hydrogenate the 2,6-diamino-3,5-dinitrotoluene, thereby producing 2,3,5,6-tetraaminotoluene ("TAT"). The TAT so produced can then be used to produce TAT salts, TAT complexes, and polybenzimidazole polymer and fibers, as described in co-pending U.S. Provisional Applications Nos. 61/138,602, 61/138,615, 61/138,626, 61/138,678, and 61/138,696, each of which is by this reference incorporated in its entirety as a part hereof for all purposes.

In a further embodiment, an integrated process is provided for preparing a complex of 2,3,5,6-tetraaminotoluene and the aromatic diacid XYTA, wherein the complex is generally described by Formula IV

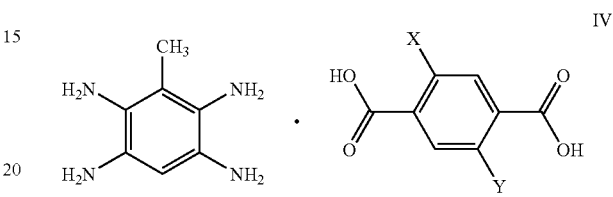

wherein X and Y are each independently selected from the group consisting of H, OH, SH, methyl, ethyl, F, Cl, and Br. This process is designed in such a way that solids handling is avoided. Filtered materials are transferred, without prior drying, in the form of suspension slurries in the solvent that is used for the respective reaction step. This integrated process design thereby avoids costly drying processes. It also avoids the handling of solid materials with possible skin sensitizing properties and toxicity, and eliminates human and environmental exposure to them.

The integrated process comprises the sequential steps under exclusion of oxygen:
a. nitration of 2,6-dichlorotoluene (V)

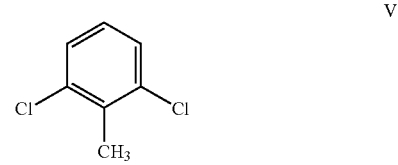

in a reaction mixture comprising oleum or SO₃, nitric acid, and H₂SO₄
wherein
(i) the concentration of nitric acid is about 2.0 to about 2.3 moles per mole of 2,6-dihalotoluene;
(ii) the concentration of SO₃ is about 1 to about 3 moles per mole of 2,6-dihalotoluene;
(iii) the concentration of 2,6-dihalotoluene in the reaction mixture is between about 12 and about 24 weight percent; and
wherein the temperature of the reaction mixture does not exceed 120° C.; thereby producing 2,6-dihalo-3,5-dinitrotoluene;
b. directly separating the 2,6-dichloro-3,5-dinitrotoluene from the reaction mixture by filtration, while recycling the sulfuric acid mother liquor;
c. washing the 2,6-dichloro-3,5-dinitrotoluene with water or acid then water, then with NH₄OH;
d. aminating the 2,6-dichloro-3,5-dinitrotoluene by forming a reaction mixture comprising a suspension of the 2,6-dichloro-3,5-dinitrotoluene in glycol in the presence of ammonia and about 2 to about 25 wt % water, and heating the reaction mixture to convert the 2,6-dichloro-3,5-dinitrotoluene to 2,6-diamino-3,5-dinitrotoluene;

e. directly separating the 2,6-diamino-3,5-dinitrotoluene from the reaction mixture formed in step (d) by filtration, washing with glycol, then washing with water;

f. forming a slurry of the 2,6-diamino-3,5-dinitrotoluene with water and transferring the slurry to a hydrogenation reactor containing a hydrogenation catalyst to form a reaction mixture;

g. hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. to hydrogenate the 2,6-diamino-3,5-dinitrotoluene, thereby producing 2,3,5,6-tetraaminotoluene;

h. contacting the 2,3,5,6-tetraaminotoluene produced in (g) with an aqueous solution comprising 1 to 6 equivalents of acid per mol of 2,3,5,6-tetraaminotoluene, optionally heating the solution, thereby dissolving the 2,3,5,6-tetraaminotoluene;

i. filtering the reaction mixture, thereby removing the spent hydrogenation catalyst;

j. combining the filtered reaction mixture with
 i. 0 to 5 equivalents of an acid;
 ii. 0 to 5 equivalents of an organic base or an inorganic base;
 iii. optionally, a buffer solution; and
 iv. an XYTA source selected from XYTA and M$_2$XYTA (Formula VI)

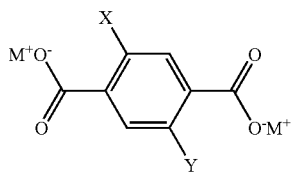

VI wherein M is K or Na,
and wherein the molar ratio of XYTA to the 2,3,5,6-tetraaminotoluene salt is from 1:1 to 1:1.1;
thereby adjusting the pH of the mixture to between about 3 and about 10 and thereby producing and precipitating the complex generally described by Formula (IV); and k. cooling, filtering, and washing the precipitated complex. Preferably, M=K and X=Y=OH.

In step (d) of the above integrated process, the reaction mixture can be formed by any of the following methods: forming a suspension of the 2,6-dichloro-3,5-dinitrotoluene in a mixture of glycol and water, then contacting the suspension with gaseous ammonia; forming a suspension of the 2,6-dichlor-3,5-dinitrotoluene in glycol, then contacting the suspension with an aqueous ammonia solution; or contacting the 2,6-dichloro-3,5-dinitrotoluene with a feed stream produced by mixing a glycol feed stream, an NH$_3$ feed stream, and a water feed stream. Using a feed stream produced by mixing a glycol feed stream, an NH$_3$ feed stream, and a water feed stream allows for easy adjustment of the relative proportions of glycol, water, and NH$_3$ at any time during the amination process.

In step (g) of the above integrated process, suitable hydrogenation catalysts comprise metal and/or metal salt; examples include without limitation Pd/C and Pt/C and mixtures thereof, optionally containing other metals from Groups VIII through X such as Fe. The groups are as described in the Periodic Table in *Advanced Inorganic Chemistry* by F. A. Cotton and G. Wilkinson, Interscience New York, 2nd Ed. (1966). Of these, Pt/C is preferred. The catalyst is typically used in the amount of about 0.5 to about 5.0 wt % metal based on 2,6-diamino-3,5-dinitrotoluene.

In step (h) of the above integrated process, any acid which allows for the dissolution of TAT in water and its subsequent re-precipitation is suitable. The selection of the acid depends on the specific needs and is based on solubility data and is easily done by one skilled in the art. Examples of suitable acids include without limitation HCl, acetic acid, H$_2$SO$_4$, and H$_3$PO$_4$. HCl is preferred, and the TAT salt generally prepared is TAT.4HCl. The solution may be heated to facilitate dissolution. Optionally, a co-solvent may be present. Examples of co-solvents include without limitation methanol, ethanol, and isopropanol. Optionally, the solution may be filtered through an absorbent material capable of adsorbing impurities. Examples of adsorbent materials include without limitation active carbon, alumina and microporous styrene.

In step (j) of the above integrated process, examples of suitable acids include without limitation HCl, acetic acid, H$_2$SO$_4$, and H$_3$PO$_4$. Examples of suitable organic bases include without limitation aliphatic amines (for example, triethylamine) and carboxylates like acetate (acetate might need to be used in conjunction with a stronger base). Examples of suitable inorganic bases include without limitation KOH, NaOH, alkali carbonates, alkali bicarbonates, and ammonia. The acids and/or bases should not form undesirable products irreversibly when added to the reaction mixture. Also, any salt byproducts produced during complex formation should be readily removable (e.g., soluble in the reaction mixture or extractable with a solvent that does not dissolve the complex).

In another embodiment of the above integrated process, a TAT salt is produced in a separate step by adding acid (for example, HCl, acetic acid, H$_2$SO$_4$, or H$_3$PO$_4$) to the filtered reaction mixture produced in step (i) followed by cooling and filtration; dissolution of the TAT salt; formation and precipitation of the TAT.XYTA complex via addition of XYTA or XYTA salt, addition of aqueous base, and cooling.

This embodiment produces higher purity TAT.XYTA complex without the need to use, e.g., carbon bed filters and allows for more flexibility in terms of production (timing) and easier dosage.

Either integrated process embodiment may also include addition of a reducing agent as described in co-pending U.S. Provisional Application No. 61/138,626.

The materials, methods, and examples herein are illustrative only and, except as specifically stated, are not intended to be limiting.

EXAMPLES

This invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

The meaning of abbreviations is as follows: "DADNT" means 2,6-diamino-3,5-dinitrotoluene, "DCDNT" means 2,6-dichloro-3,5-dinitrotoluene, "g" means gram(s), "GC" means gas chromatography, "L" means liter(s), "mL" means milliliter(s), and "mol" means mole(s) or molar.

Materials.

2,6-dichloro-3,5-dinitrotoluene (>99% purity) was prepared by nitration of 2,6-dichlorotoluene as described in copending U.S. Provisional Application No. 61/138,615.

Example 1

Preparation of DADNT from DCDNT

To a 22-L 4-neck Morton style round bottom glass reaction vessel equipped with external ice cooling, mechanical stirrer, addition funnel, $N_2$ inlet and outlet, and thermometer was added suspend 2315.0 g DCDNT (9.22 mol, 1 equiv) in 14.5 L ethylene glycol at room temperature, to form a yellow slurry. The reaction vessel was purged with nitrogen while heating the yellow slurry to 150° C. When the reaction temperature reached about 120° C., the mixture became a greenish-yellow solution. After reaching 145° C.-150° C., ammonia addition was begun. A total of 1000 g ammonia (58.32 mol, 6.38 equiv) was added over 9.5 hours.

The reaction slurry was cooled to 60° C.-65° C., filtered, and washed successively with warm (60° C.) ethylene glycol (2×1000 mL), water (2×1000-mL) and methanol (3×1000 mL). The cake was dried at room temperature under nitrogen overnight. Yield: 1883.4 g sand textured, bronze colored solids. Purity by GC analysis: 96.4%.

Unless otherwise defined, all technical and scientific terms used herein have the same meaning as commonly understood by one of ordinary skill in the art to which this invention belongs. In case of conflict, the present specification, including definitions, will control.

Although methods and materials similar or equivalent to those described herein can be used in the practice or testing of the present invention, suitable methods and materials are described herein.

Unless stated otherwise, all percentages, parts, ratios, etc., are by weight.

When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

When the term "about" is used in describing a value or an end-point of a range, the disclosure should be understood to include the specific value or end-point referred to.

As used herein, the terms "comprises," "comprising," "includes," "including," "containing," "characterized by," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Use of "a" or "an" are employed to describe elements and components of the invention. This is done merely for convenience and to give a general sense of the invention. This description should be read to include one or at least one and the singular also includes the plural unless it is obvious that it is meant otherwise.

It is to be appreciated that certain features of the invention which are, for clarity, described above and below in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range.

What is claimed is:

1. A process for preparing 2,6-diamino-3,5-dinitrotoluene (Formula I),

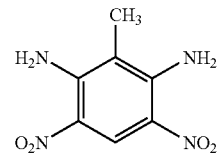

comprising, under exclusion of oxygen, providing a reaction mixture comprising a suspension of 2,6-dihalo-3,5-dinitrotoluene (Formula III)

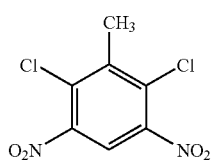

in glycol in the presence of ammonia and about 2 to about 25 wt % water, and heating the reaction mixture in the range of about 100° C. to about 160° C. to convert the 2,6-dichloro-3,5-dinitrotoluene to 2,6-diamino-3,5-dinitrotoluene.

2. The process of claim 1 wherein the reaction mixture is provided by forming a suspension containing about 10 to about 25 wt % 2,6-dichloro-3,5-dinitrotoluene in a mixture of glycol and about 2 to about 25 wt % water; and the suspension is contacted with gaseous $NH_3$ to convert the 2,6-dichloro-3,5-dinitrotoluene to 2,6-diamino-3,5-dinitrotoluene.

3. The process of claim 1 wherein the reaction mixture is provided by forming a suspension containing about 10 to about 25 wt % 2,6-dichloro-3,5-dinitrotoluene in glycol and contacting the suspension with an aqueous ammonia solution to form a reaction mixture wherein water is present at about 2 to about 25 wt %; and the reaction mixture is heated to a temperature in the range of about 100° C. to about 160° C. to convert the 2,6-dichloro-3,5-dinitrotoluene to 2,6-diamino-3,5-dinitrotoluene.

4. The process of claim 1 wherein the reaction mixture is provided by contacting the 2,6-dichloro-3,5-dinitrotoluene with a feed that contains glycol, NH3, and about 2 to about 25 wt % water, to form a reaction mixture which is a suspension containing about 10 to about 25 wt % 2,6-dichloro-3,5-dinitrotoluene; and the reaction mixture is heated to a temperature in the range of about 100° C. to about 160° C. to convert the 2,6-dichloro-3,5-dinitrotoluene to 2,6-diamino-3,5-dinitrotoluene.

5. The process of claim 1 further comprising the step of hydrogenating the 2,6-diamino-3,5-dinitrotoluene by (i) forming a slurry of the 2,6-diamino-3,5-dinitrotoluene with water, and (ii) contacting the slurry with a hydrogenation catalyst and hydrogen at a pressure in the range of about 0.31 to about 3.45 MPa and a temperature in the range of about 20° C. to about 100° C., to hydrogenate the 2,6-diamino-3,5-dinitrotoluene, thereby producing 2,3,5,6-tetraaminotoluene.

* * * * *